United States Patent [19]

Weterings

[11] 3,963,793

[45] June 15, 1976

[54] PROCESS FOR PREPARING DEHYDRODIMERIZATION PRODUCTS

[75] Inventor: Cornelis A. M. Weterings, Stein, Netherlands

[73] Assignee: Stamicarbon B.V., Geleen, Netherlands

[22] Filed: Dec. 18, 1974

[21] Appl. No.: 534,100

[30] Foreign Application Priority Data

Dec. 18, 1973 Netherlands.................. 7317293

[52] U.S. Cl. .................. 260/668 R; 260/668 C; 260/668 D; 260/465.8 D; 260/561 R; 260/290 R; 260/537 R; 260/680 R; 252/462; 252/475

[51] Int. Cl.² ................. C07C 15/18; C07C 11/12

[58] Field of Search ........ 260/668 D, 680 R, 668 R, 260/405.8 D, 668 C, 561 R, 290 R, 537 R, 668 C

[56] References Cited
UNITED STATES PATENTS

| | | | |
|---|---|---|---|
| 3,631,216 | 12/1971 | Lipsig............................. | 260/680 R |
| 3,730,957 | 5/1973 | Bozik et al....................... | 260/673 |
| 3,761,536 | 9/1973 | Bozik et al....................... | 260/673;680 R |

FOREIGN PATENTS OR APPLICATIONS 1,259,766   1/1972   United Kingdom................ 260/680

*Primary Examiner*—D. Horwitz
*Attorney, Agent, or Firm*—Cushman, Darby & Cushman

[57] ABSTRACT

The invention relates to catalytic dehydrodimerization of compounds of the formula $CH_3$—R wherein R represents a group which is not reactive under the reaction conditions and is bonded to the methyl group by a carbon atom connected to an adjacent atom by an unsaturated bond, by catalysts, including bismuth trioxide, thallium trioxide or mixtures thereof, which are supported on basic carrier materials of high surface area.

18 Claims, No Drawings

3,963,793

PROCESS FOR PREPARING DEHYDRODIMERIZATION PRODUCTS

The invention relates to a process for the dehydrodimerization of compounds of the general formula $CH_3-R$, where R represents a group that is not reactive under the reaction conditions and is bonded to the methyl group by a carbon atom connected to an adjacent atom by an unsaturated bond. In particular the invention relates to a process for dehydrodimerization of compounds $CH_3-R$ by catalysts based on thallium trioxide and/or bismuth trioxide.

BACKGROUND OF THE INVENTION

U.S. Pat. No. 3,494,956 discloses that dehydrodimerization products of propene, isobutene, toluene, methyl styrene, acetonitrile, and acetic acid may be obtained by allowing substances to react with oxygen in the vapour phase at temperatures of over 300°C and in the presence of lead oxide and/or cadmium oxide, and/or thallium oxide. However, in the presence of optimum reaction conditions, considerable amounts of starting materials in this known process will react with the oxygen present to form carbon dioxide, with adverse affects on yields of products.

U.S. patent application Ser. No. 812,415, filed Apr. 1, 1969 now abandoned discloses that propene, toluene, and acetic acid, and the like, may be converted into their respective dehydrodimerization products by oxidative coupling in the presence of a regeneratable reagent containing oxygen, e.g. bismuth trioxide, in the absence of oxygen. In the coupling reaction, the oxygen of the regeneratable reagent is consumed, so that the exhausted reagent must be regenerated by oxidation in the absence of organic starting material.

In this known process, it is necessary to employ a carrier (alundum, silica, carborundum, dolomite, zirconia, alumina) which has a small specific surface area, preferably smaller than 1 $m^2/g$, as the reaction will, otherwise, proceed with little selectively.

It has now been found that the above-mentioned dehydrodimerization products may be obtained in high yields by oxidative coupling in the absence of oxygen gas, if the catalyst to be used is supported on a basic carrier with a large surface area.

SUMMARY OF THE INVENTION

The invention consequently relates to a process for the catalytic dehydrodimerization of compounds of the general formula $CH_3-R$, where R represents a group that is not reactive under the reaction conditions and is bonded to the methyl group by a carbon atom connected to an adjacent atom by an unsaturated bond, by means of catalysts based on thallium trioxide and/or bismuth trioxide, in particular said process is characterized in the aforementioned catalysts are supported on a basic carrier with a large surface area.

DETAILED DESCRIPTION OF THE INVENTION

In accordance with the invention, compounds of the $CH_3-R$, wherein R is not reactive under the reaction conditions and is bonded to the methyl group by a carbon atom connected to an adjacent atom by an unsaturated bond are contacted with dehydromerization catalysts at elevated temperatures, said catalyst being thallium trioxide, bismuth trioxide or mixtures thereof and said catalyst supported on basic carrier materials of high surface areas. Reactants of the formula $CH_3-R$ are thereby dehydrodimerized. By dehydrodimerization is meant that the compounds $CH_3-R$ are dimerized and that the dimerized products are unsaturated as by dehydrogenation.

As set forth above the reactants are of the formula $CH_3-R$, wherein R is a group that is not reactive under the conditions of dehydrodimerization. "By not reactive under the conditions of the dehydrodimerization" is meant that the R group will not dimerize or react with itself and that the R group will not dehydrogenate. Obviously, if the R group could, practically, dimerize with itself or dehydrogenate, such side reactions would interfere with the process of the invention.

The R group of compound $CH_3-R$ is also defined as bonded to the methyl group ($CH_3-$) by a carbon atom connected to an adjacent atom by an unsaturated bond. The term "unsaturated bond" comprises not only olefinically unsaturated bonds, but also a double bond forming part of an aromatic ring, a heterocyclic ring, a carbon-oxygen bond

a carbon-nitrogen bond $-C\equiv N$, and a carbon-carbon triple bond $-C\equiv C-$.

Various compounds of the formula $R-CH_3$, or $CH_3-R$, may be suitable for dehydrodimerization according to the invention. Olefins with at least 3 C-atoms, such as propene, butenes, pentenes, and hexenes, including iso-pentenes and iso-hexenes may be dehydrodimerized. In addition alkyl-substituted and alkenyl-substituted benzenes, including toluene, xylenes, and methyl styrene may be hydrodimerized. As mentioned above as in prior art dehydrodimerization processes, compounds such as acetic acid, acetonitrile, N,N-dimethyl acetamide, picoline and methyl acetylene may be subjected to the dehydrodimerization process of the invention.

The catalytic material used in accordance with the process of the invention comprises a catalyst of thallium trioxide or bismuth trioxide on support material which is a basic support material of high surface area. Within the scope of the invention, is the use of a mixture of thallium trioxide and bismuth trioxide, as the catalyst, on a basic support material of high surface areas.

A suitable basic carrier with a large surface area is magnesium oxide. Carriers suitable for use in the process according to the invention are the oxides of elements of Group II of the Periodic Table of Elements including beryllium, calcium, strontium, and barium, as well as magnesium. The size of the surface area, measured by the BET-method, as described in J. Am. Chem. Soc. 60, 309 (1938), must be at least 20 $m^2/g$, and preferably more than 50 $m^2/g$. The surface area of the basic carrier may range from 100 to 200 $m^2/g$. If the surface area of the carrier is less than 20 $m^2/g$, the surface area of the catalytically active oxides supported on the carrier will also be correspondingly lower and, hence, comparatively little oxygen will be available for the coupling reaction.

It has also been found that thallium trioxide and bismuth trioxide on a magnesium-oxide carrier can be rendered more active as dehydrodimerization catalysts, if these catalysts contain some silver. The amount of silver may vary between 1 and 50% by weight, based on the metal oxide. By preference, the catalysts contain about 30% by weight of silver, based on the catalytically active metal oxide. The result of the addition of silver to the $Tl_2O_3/MgO$ and $Bi_2O_3/MgO$ catalysts is that the reaction can be carried out at temperatures of about 300°–400°C, in particular of about 350°C with high yields.

The latter fact is surprising, since it is known from the disclosure in U.S. Pat. application Ser. No. 812,415, filed Apr. 1, 1969, that $Bi_2O_3$ does not show high catalytic activity below temperatures of about 500°C. $Tl_2O_3$ is known to decompose at temperatures of over 400°C to form $Tl_2O$, which is volatile at this temperature, and is known to have little activity as a dehydrodimerization catalyst in the known processes.

The catalyst may be prepared by wetting the carrier, e.g. magnesium-oxide powder, with a mixture of equal parts of glycol and water, and by adding to this mixture a solution that contains a soluble salt of bismuth and/or thallium and a soluble silver salt and which has been acidified to a pH of about 3. By soluble salt is meant nitrates, although acetates or other salts which are soluble in water and decompose upon heating may be employed. The resulting mixture is evaporated, dried at about 150°C, processed into tablets, if so desired, and then calcinated at a temperature between 400° and 550°C for some hours. The amount of catalytically active material and promoter put on the carrier may vary within wide limits e.g. the catalyst may be between 10 and 80 % by weight of the carrier. Preferably, the catalyst comprises about 50 % by weight of the carrier.

The splitting off of hydrogen in the dimerization is effected by means of the oxygen present in the catalytically active oxide material. Although small amounts of free molecular oxygen may be present during the coupling reaction in the process according to the invention, preferably, oxygen and air are excluded from the reaction process since oxygen will convert the starting material to carbon dioxide, which results in reduced yields of dehydrodimerization products.

The dimerization may be effected with the aid of a fluidized or a fixed catalyst.

If use is made of a fluidized catalyst, the gaseous starting material serves as the fluidizing gas. If so desired, this starting material may be diluted with an inert gas, such as $N_2$, steam, or lower alkanes.

The pressure at which the reaction is effected is not critical. By preference, use is made of a low superatmospheric pressure to overcome the resistance met with by the gas in the reactor.

Once the catalyst that is poor in oxygen or exhausted by the process, it may be regenerated by treating it with a gas containing molecular oxygen. The regeneration may be effected in the dimerization reactor itself, or it is possible to discharge the catalyst from the reactor, carrying out the oxygen treatment in a separate zone and recycling the catalyst. The regeneration of the catalyst poor in oxygen may take place at the same temperature as that at which the coupling reaction is effected. However, it is also possible to carry out the regeneration at elevated temperature, which shortens the required regeneration time. In the regenerative treatment, no oxygen is bound by the silver contained in the catalyst.

In a continuous reaction in the presence of molecular oxygen, the efficacy of the catalyst can be characterized by the conversion and selectivity obtained at a given space velocity, since these quantities are constant. In a cyclic process, where the oxygen of the metal oxide is used, these quantities are not constant. The conversion passes a maximum value and falls to zero when the total amount of oxygen contained in the metal oxide and available for the reaction has been consumed. The selectivity likewise varies with the degree of exhaustion of the catalytically active oxide. Hence, to judge the efficacy of the catalysts, the average conversion and selectivity attained per cycle may be determined. To this end, the period of time of the entire cycle is not necessarily considered, but rather the time period during which economic and relatively large production scale is still possible is considered. The values given in the examples relate to a cycle time in which the concentration of desired product in the vent gas has fallen to ⅓ part of the maximum concentration during the cycle. "Average conversion" denotes:

$$\frac{\text{total amount of starting material converted}}{\text{total amount of starting material}} \times 100\%$$

"Selectivity" denotes:

$$\frac{\text{number of g. moles of starting material converted into desired reaction product}}{\text{total number of g. moles of starting material converted}} \times 100\%$$

In the embodiments described below, the dehydrodimerization was carried out in the absence of molecular oxygen. The starting material and air were passed alternately through the catalyst bed. In all experiments it was observed that different results were always obtained in the first few exhaustion cycles. After some experiments a stable level was reached. The results given in the examples always relate to experiments carried out after the stable end level had been reached.

The dimerized products have various utilities. The dehydrodimerization products obtained from olefinic starting materials may be used as non-conjugated diene monomers in the preparation of EPDM (ethylene-propylene-nonconjugated diene terpolymers), as comonomers in the polymerisation of e.g. acrylic acid esters, as solvents, and as synthetic intermediates.

The dehydrodimerisation product of acetonitrile, acetic acid or derivatives thereof may produce succinic acid, a starting material for e.g. polyesters. Dibenzyl, the polymerisation product of toluene, may be used as a solvent or heat transfer medium or may be converted to stilbene.

EXAMPLE 1

A glass reactor with an internal diameter of 2.2 cm was filled with 50 cm³ of catalyst granules. The weight of the catalyst was 72 grams. The temperature of the reactor was controlled by means of an electrically heated fluid bed of carborundum particles. The catalyst, bismuth trioxide supported on magnesium oxide, contained 23.4 % by weight of $Bi_2O_3$. The BET surface area of the carrier material was 144 m²/g. From electron microscopy, the external surface area of the $Bi_2O_3$ can be calculated to be 32 m²/g $Bi_2O_3$. By means of this catalyst bed, a cyclic process was carried out by alternately passing propene and air through the bed at 500°C with a space velocity of 210 and 1000 hours⁻¹, respectively. The feed of propene was terminated after the 1,5-hexadiene concentration in the vent gas had fallen to ⅓ of the maximum 1,5-hexadiene concentration during the cycle. The catalyst was subsequently re-oxidized with oxygen from the air during 10 minutes. The time of the exhaustion cycle was 24 minutes. The average conversion was 19.8%, with selectivities towards 1,5-hexadiene, cyclohexadiene, and benzene of 64%, 7%, and 16%, respectively. 13% of the toluene converted was converted to carbon dioxide and water.

EXAMPLE 2

The experiment described in Example 1 was repeated, but with bismuth trioxide supported on an acid carrier. The carrier used was silicon dioxide with a surface area of 204 m²/g. 50 cm³ of catalyst granules with 26.5% by weight of $Bi_2O_3$ were put in the reactor. The external surface area of the bismuth trioxide was 27 m²/g. The space velocity was 200 hours⁻¹. The temperature was mainted at 500°C. The time of the exhaustion cycle was 49 minutes.

The average conversion amounted to 7.8% with selectivities towards 1,5-hexadiene, cyclohexadiene, and benzene of 53%, 6%, and 14%, respectively. 27% of the propene converted was converted to carbon dioxide and water.

EXAMPLE 3

The experiment described in Example 1 was repeated, but at a reaction temperature of 350°C. The time of the exhaustion cycle was 35 minutes. The average conversion was 5.6% with selectivities towards 1,5-hexadiene, cyclohexadiene, and benzene of 89%, 5%, and 2%, respectively. 4% of the propene converted was converted to carbon dioxide and water.

EXAMPLE 4

The experiment described in Example 3 was repeated, but this time 50 cm³ (78 grams) of a silver-promoted bismuth-trioxide catalyst on magnesium oxide was put in the reactor. The catalyst contained 20.6% by weight of $Bi_2O_3$ an 8.7% by weight of Ag.

The BET surface area of the magnesium oxide was 144 m²/g. The time of the exhaustion cycle was 27 minutes, and the average conversion 18.7% with selectivities towards 1,5-hexadiene cyclohexadiene, and benzene of 90%, 5%, and 3%, respectively. The amount of propene converted into carbon dioxide and water was 2%.

EXAMPLE 5

The experiment described in Example 3 was repeated, but this time 50 cm³ (83 grams) of a silver-promoted thallium-trioxide catalyst on magnesium oxide (BET surface 144 m²/g) was put in the reactor. The catalyst contained 21.3% by weight of $Tl_2O_3$ and 6.9% by weight of Ag. The time of the exhaustion cycle was 30 minutes. The average conversion was 23.2%, with selectivities towards 1,5-hexadiene, cyclohexadiene, and benzene of 93%, 4%, and 1.5%, respectively. 1.5% of the propene converted was converted to carbon dioxide and water.

EXAMPLE 6

The experiment described in Example 5 was repeated, but toluene was used instead of propene. The toluene was passed through the catalyst at 350°C with a space velocity of 200 hours⁻¹. The time of the exhaustion cycle was 37 minutes. The average conversion was 17.8%. The selectivity towards bibenzyl (1,2-diphenyl ethane) was 99%. 1% of the toluene converted was converted to carbon dioxide and water.

EXAMPLE 7

The experiment described in Example 4 was repeated, but, instead of propene, isobutene was passed through at 350°C with a space velocity of 200 hours⁻¹. The time of the exhaustion cycle was 31 minutes; the average conversion 16.9% with selectivities towards 2,5-dimethyl-1,5-hexadiene, 1,4-dimethyl-1,3-cyclohexadiene, and p-xylene of 88%, 6%, and 3%, respectively. 3% of the isobutene converted was converted to carbon oxides and water.

What is claimed is:

1. In a process for dehydrodimerization compounds of the formula $CH_3$—R,
    wherein R represents a group that is not reactive under the dehydrodimerization reaction: wherein R contains a carbon atom which is unsaturated, wherein $CH_3$— and R are attached to each other by bonding of said methyl group to said unsaturated carbon atom;
    comprising contacting $CH_3$—R with a dehydrodimerization catalyst at elevated temperatures,
    the improvement comprising, contacting R—$CH_3$ at temperatures between 300°–400°C with a catalytic composition comprising a catalyst on a support, wherein said catalyst is thallium trioxide, bismuth trioxide or mixtures thereof; said support comprising an oxide of an element of Group II of the Periodic Table of Elements and having a surface area of at least 20 m²/g wherein the catalyst comprises 10–80% by weight of the support.

2. The improvement of claim 1 wherein said surface area is over 50 m²/g.

3. The improvement of claim 1 wherein said carrier material is magnesium oxide.

4. The improvement of claim 1 wherein said catalytic composition contains silver as a promoter in an amount of 1 to 50% by weight based on the catalyst.

5. The improvement of claim 4 wherein the combined amount of catalyst and promoter is 10–80% by weight of the carrier.

6. The improvement of claim 5 wherein said combined amount of catalyst and promoter is 50% by weight of said carrier.

7. The improvement of claim 2 characterized in that 1,5-hexadiene is prepared by dehydrodimerization of propene.

8. The improvement of claim 2 characterized in that 2,5-dimethyl-1,5-hexadiene is prepared by dehydrodimerization of isobutene.

9. The improvement of claim 2 characterized in that 1,2-diphenyl ethane is prepared by dehydrodimerization of toluene.

10. A process for dehydrodimerization compounds of the formula $CH_3$—R,
    wherein R represents a group that is not reactive under the dehydrodimerization reaction: wherein R contains a carbon atom which is unsaturated, wherein $CH_3$— and R are attached to each other by bonding of said methyl group to said unsaturated carbon atom; said process comprising
    providing a support-catalyst composition wherein said catalyst is thallium trioxide, bismuth trioxide or mixtures thereof and said support is an oxide of an element of Group II of the Periodic Table of Elements and has a surface area of over 20 m²/g, wherein said catalyst is 10–80% by weight of the support; and contacting $CH_3$—R with the supported catalyst at temperatures between 300° to 400°C.

11. The process of claim 10 wherein said $CH_3$—R is an olefin of at least 3 carbon atoms.

12. The process of claim 10 wherein $CH_3$—R is an alkyl substituted or an alkenyl substituted benzene, said alkyl and alkenyl containing one to four carbon atoms.

13. The process of claim 10, wherein said element is beryllium, calcium, strontium, barium or magnesium.

14. The process of claim 10, wherein said catalyst is thallium oxide.

15. The process of claim 14, wherein said thallium oxide is admixed with bismuth trioxide.

16. The process of claim 14, wherein said catalyst contains silver as a promoter in an amount of 1 to 50% by weight based on said catalyst.

17. The process of claim 15, wherein said catalyst contains silver as a promoter in an amount of 1 to 50% by weight based on the catalyst.

18. The improvement of claim 1, wherein R—$CH_3$ is an olefin of at least 3 carbon atoms, an alkyl-substituted benzene or an alkenyl-substituted benzene, each of said alkyl and alkenyl containing 1 to 4 carbon atoms.

* * * * *